United States Patent
Miltner et al.

(10) Patent No.: US 9,052,293 B2
(45) Date of Patent: Jun. 9, 2015

(54) TEST METHOD AND TEST DEVICE FOR ANALYSING A BODY FLUID

(75) Inventors: Karl Miltner, Frankenthal (DE); Robert Lorenz, Worms (DE); Ulrich Porsch, Weinheim (DE); Clemens Knapp, Viernheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 13/209,708

(22) Filed: Aug. 15, 2011

(65) Prior Publication Data

US 2012/0010489 A1    Jan. 12, 2012

Related U.S. Application Data

(63) Continuation of application No. PCT/EP2010/052012, filed on Feb. 18, 2010.

(30) Foreign Application Priority Data

Feb. 18, 2009   (EP) ..................................... 09153113

(51) Int. Cl.
*G01N 21/77*      (2006.01)
*G01N 21/84*      (2006.01)
(Continued)

(52) U.S. Cl.
CPC ...... *G01N 21/8483* (2013.01); *G01N 35/00009* (2013.01); *G01N 2021/8488* (2013.01); *G01N 2021/8494* (2013.01); *G01N 2035/0491* (2013.01)

(58) Field of Classification Search
CPC ............. A10B 12/006; G01N 21/8483; G01N 33/4875
USPC .................................. 436/164, 169; 600/365
See application file for complete search history.

(56) References Cited

U.S. PATENT DOCUMENTS

| | | | |
|---|---|---|---|
| 3,526,480 | A | 9/1970 | Findl et al. |
| 4,313,735 | A | 2/1982 | Yamashita et al. |
| 5,051,901 | A | 9/1991 | Endo |

(Continued)

FOREIGN PATENT DOCUMENTS

| | | |
|---|---|---|
| CA | 2736324 | 4/2010 |
| EP | 0 256 806 A2 | 2/1988 |

(Continued)

OTHER PUBLICATIONS

Translation of International Preliminary Report on Patentability, International Application No. PCT/EP2010/052012, 11 pages.

*Primary Examiner* — Jill Warden
*Assistant Examiner* — Dwayne K Handy
(74) *Attorney, Agent, or Firm* — Roche Diabetes Care, Inc.

(57) ABSTRACT

There is provided a test method for analysing a body fluid in which a test tape is used in a test device in order to successively provide analytical test fields stored on the test tape, wherein body fluid is applied by a user to the test field provided at a time and the said test field is photometrically scanned using a measuring unit of the device to record measurement signals. In order to increase the measurement reliability, it is proposed that a control value is determined from a time-dependent and/or wavelength-dependent change in the measurement signals and that the measurement signals are processed as valid or discarded as erroneous depending on the control value.

3 Claims, 2 Drawing Sheets

(51) Int. Cl.
 *G01N 35/00* (2006.01)
 *G01N 35/04* (2006.01)

(56) References Cited

U.S. PATENT DOCUMENTS

| | | | |
|---|---|---|---|
| 5,304,468 A | 4/1994 | Phillips et al. | |
| 5,605,837 A * | 2/1997 | Karimi et al. | 436/14 |
| 6,151,110 A | 11/2000 | Markart | |
| 6,458,596 B1 | 10/2002 | Poellmann | |
| 2005/0201897 A1 | 9/2005 | Zimmer et al. | |
| 2006/0216817 A1 | 9/2006 | Hoenes et al. | |
| 2006/0240403 A1 | 10/2006 | List et al. | |
| 2006/0243031 A1 | 11/2006 | Kondo et al. | |
| 2007/0217950 A1 | 9/2007 | Kramer et al. | |

FOREIGN PATENT DOCUMENTS

| | | |
|---|---|---|
| EP | 1128178 A1 | 8/2001 |
| EP | 1 873 515 A1 | 1/2008 |
| JP | 05-256783 A | 10/1993 |
| JP | 07-026964 B | 3/1995 |
| WO | WO 93/12422 | 6/1993 |
| WO | WO 99/18426 | 4/1999 |
| WO | 2004/047642 A1 | 6/2004 |
| WO | WO 2005/032372 A1 | 4/2005 |

* cited by examiner

TEST METHOD AND TEST DEVICE FOR ANALYSING A BODY FLUID

CROSS-REFERENCE TO RELATED APPLICATIONS

This application is a continuation of International Application No. PCT/EP2010/052012 filed Feb. 18, 2010, which claims priority to EP Application No. 09153113.7 filed Feb. 18, 2009. Each of the referenced applications is incorporated herein by reference in its entirety.

FIELD OF THE INVENTION

The invention concerns a test method for analysing a body fluid in particular for blood sugar determination in which a test tape preferably in the form of a tape cassette is used in a test device in order to successively provide a plurality of analytical test fields stored on the test tape by means of tape transport, wherein body fluid is applied by a user to the test field provided at a time and the said test field is photometrically scanned using a measuring unit of the device to record measurement signals. The invention additionally concerns a corresponding test device.

BACKGROUND

A generic test tape device is for example known from the EP application No. 08166955.8 of the applicant. It describes a tape cassette with a test tape on which positioning markers are located in addition to the analytical test fields in order to ensure a reliable positioning in various functional positions for each relevant tape section.

A method for detecting erroneous positioning of a test strip that can be analysed by optical means which is based on the comparison of two measured values from measurement spots spaced apart from one another in the insertion direction of the test strip in a test device is known from DE 199 32 846 A1. However, the conditions in test strip systems are hardly comparable with tape systems in so far as the test strips are inserted individually into a device guide, whereas tape transport and tape guidance is effected by the consumable itself.

What is needed therefore is to further improve the test methods and devices proposed in the prior art and ensure an increased security against operating errors and measuring errors.

SUMMARY

A first aspect of the invention is based on the idea of deducing an error analysis from an expected signal change of a measurement signal relevant for the test result. Accordingly it is proposed that a control value is determined from a time-dependent and/or wavelength-dependent change of the measurement signals and that the measurement signals are processed as valid or discarded as erroneous depending on a preset threshold value of the control value. In this manner it is possible to substantially exclude falsifying external effects on the measurement result. It is also possible to check several potential faults in parallel.

An error discrimination based on the circumstances of the sample application provides that the measurement signals are recorded at two different wavelengths and that the control value is determined from a signal difference of the measurement signals at different wavelengths, wherein a fault is detected by the device and optionally an error signal is triggered when the signal difference disappears. This also in particular allows those manipulations to be detected in which a user for example presses his finger against the test field without applying a sample.

The signal difference of the measurement signals at different wavelengths is advantageously based on the wetting of the provided test field with the body fluid so that it is possible to reliably detect errors even at low analyte concentrations. In this connection it is advantageous when the measurement signals at different wavelengths are obtained in the visible wavelength range and in the infrared range.

Another advantageous embodiment is that the control value is determined from a signal difference of the measurement signals recorded at the beginning and end of a measurement interval, wherein a fault is detected when the signal difference disappears. This type of error recognition is based on the special reaction kinetics of an analyte on test fields that change colour which can thus be distinguished from a mechanical tape manipulation.

According to a further advantageous embodiment the measurement signals are recorded over the duration of a measurement interval and the control value is determined from a change in the measurement signal in an initial period of the measurement interval and a fault is detected when the change in measurement signal is below a preset minimum value. This also allows environmental effects to be excluded which, in comparison with a regular measurement, only result in a considerably reduced initial signal change.

In the preparation phase for liquid application it is advantageous when blank values are recorded cyclically on the test field that is provided, and when the control value is determined from a change in the blank value compared to an initial blank value, wherein an application of liquid is determined when the change in blank value is above the threshold value and a fault is determined when it is below the threshold value.

The current blank value is advantageously taken into consideration for determining a relative measurement value for an analyte in the body fluid in the case of a change in the blank value up to a preset limit value. This allows one to obtain a referenced measurement value without slight changes in the reference quantity resulting in a falsified result.

The aforementioned advantages also result for a corresponding device for carrying out the method according to the invention.

Another aspect of the invention is that a lot control value is stored on a storage medium assigned to the test tape, that a test field control value is determined from a blank measurement of the yet unused first test field, and that the usability of the first test field is determined by comparing the lot control value and the test field control value. Such a quality check enables damaging effects on the test material which is for example only used as a consumable after a long period of storage, to be detected. As a result of this check, it is also possible to rate the entire test tape as being unusable if the test field control value of the first test field on the test tape deviates by more than a specified tolerance from the lot control value.

The lot control value is advantageously determined during a batchwise production of test tapes by measurement of test fields and calibration fields on the test tape material. This can be reliably carried out when producing tests in a tape form due to the homogeneous processing processes.

In order to allow for a change that can be tolerated for subsequent measurements, it is advantageous when the test field control value of a test field of the test tape that has been provided and rated as usable is stored in the device as a new tape control value, and when the test field control value correspondingly determined of the next test field is compared with the stored tape control value for a check of the usability of the next test field.

An advantageous measured value referencing can be achieved by carrying out a calibration measurement by detecting a preferably white calibration field associated with the respective test field by means of the measuring unit, and determining the test field control value as a relative value from the blank measurement and the calibration measurement.

It is advantageous for a substantially automatic processing when the lot control value is stored in a storage means, preferably in an RFID chip, applied to the tape cassette so that a comparison can be carried out by the device without further user interaction.

Another aspect of the invention is also that a signal offset of the measuring unit is recorded in a reference area of the test tape associated with the provided test field and that when the signal offset exceeds a specified threshold value, an error indication is triggered. This allows contamination or other changes in the optical path to be reliably detected.

Another aspect provides that the signal offset is detected on a dark coloured black field as a reference area of the test tape, where the black field is arranged on a section of tape adjacent to the respective test field and is positioned by tape transport in the detection area of the measuring unit.

BRIEF DESCRIPTION OF THE DRAWINGS

The invention is further elucidated in the following on the basis of the embodiment example shown in the drawing.

DETAILED DESCRIPTION

Figure 1:
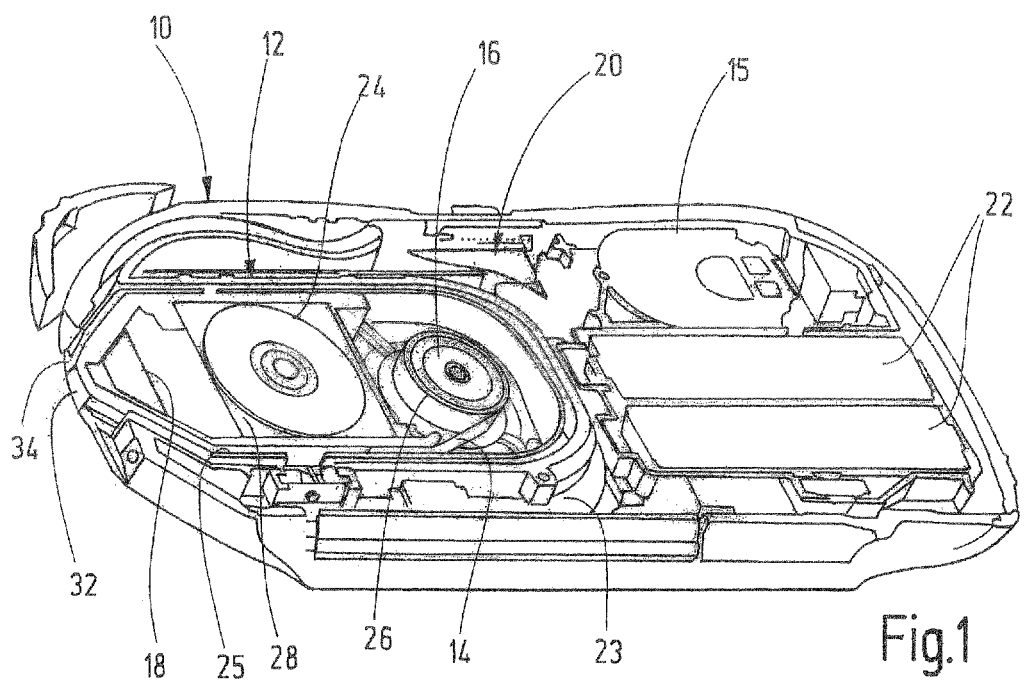
FIG. 1 shows an analytical test tape system for blood sugar determination comprising a hand-held device and a test tape cassette in a cut open perspective view.

The test tape system shown in FIG. 1 enables the use of a tape cassette 12 with a test tape 14 that can be wound forwards as a consumable in a hand-held device 10 for carrying out glucose tests, where function checks are carried out in various phases of the measurement process. The general principle of the device is described in the EP application No. 02026242.4 which is incorporated herein by reference.

The hand-held device 10 has a tape drive (motor 15 with drive spindle 16), a measuring unit 18, a microprocessor-assisted control device 20 and an energy supply 22. A display that is not shown enables the output of measurement results and device messages for the user.

The tape cassette 12 that can be inserted into a receiving compartment 23 of the device 10 comprises a supply spool 24 for unused test tape 14 and a take-up spool 26 for used test tape that can be coupled to the drive 16 as well as a tape guide 25 with a deflecting tip 34. The supply spool 24 is arranged in a storage chamber 28 that is sealed against the environment.

The test tape 14 is provided in sections with test fields 32 which are thus arranged in a given sequence in the direction of tape transport. In this connection it should be taken into consideration that the test fields 32 contaminated with blood are disposed of on the take-up spool 26 and hence it is not feasible to rewind the tape.

The front side of the test field 32 that is provided or active in each case can be loaded with sample liquid, in particular blood or tissue fluid, in the area of the deflecting tip 34 which is accessible from outside. The analyte (glucose) is detected by a reflection-photometric detection of a colour change of the test fields 32 from the rear side by means of the measuring unit 18. For this purpose the test fields 32 are applied to a transparent carrier foil as a dry reagent layer. The test fields 32 can be successively brought into use by appropriately advancing the tape. In this manner it is possible to carry out multiple tests for patient self-monitoring without having to frequently replace the consumables.

Figure 2:
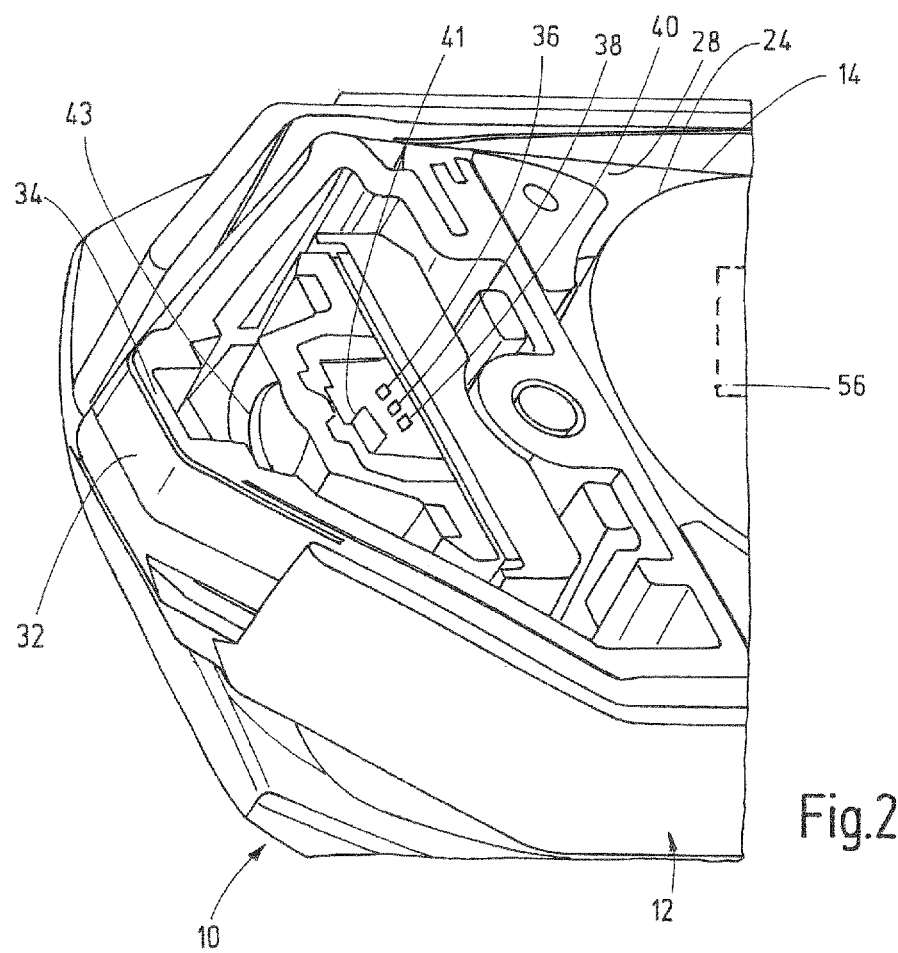
FIG. 2 shows an enlargement of a section of FIG. 1 in the area of a measuring tip.

As shown in FIG. 2 the measuring unit 18 fixed permanently in the device and engaging in the cassette 12 has three light-emitting diodes 36, 38, 40 as a radiation source and a photodiode 41 as a detector for a reflection-photometric signal detection. An optical system 43 provides a focussed optical path with imaging of light spots of defined size and intensity on the rear side of the tape. The middle light-emitting diode 38 radiates in the visible (red) wavelength range at about 650 nm, whereas the outer light-emitting diodes 36, 40 work in the infrared range at 875 nm. The light scattered backwards on the test strip 48 is detected at a specified time interval using the photodiode 41.

Figure 3:
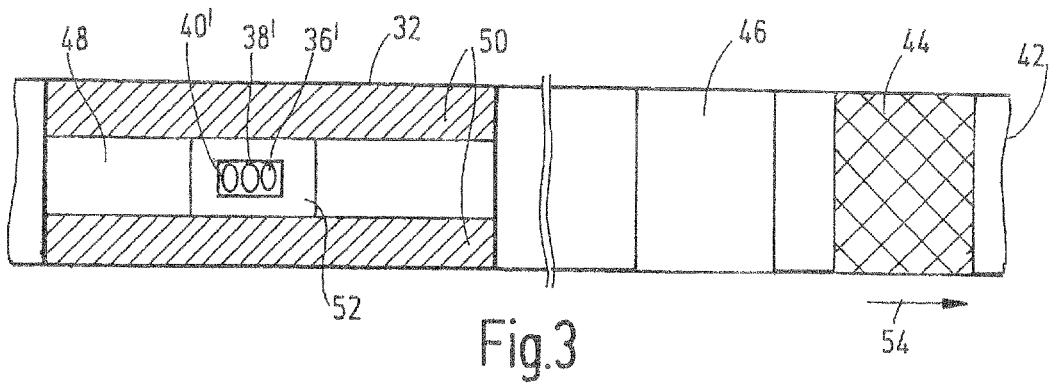
FIG. 3 shows a test tape section in a top view.

As shown in FIG. 3 spaced apart test fields 32 are each located individually on an allocated tape section 42 which is additionally provided with further check or control fields in the form of a black field 44 and a white field 46. The test field 32 has a central test strip 48 formed by the test chemistry layer which is laterally delimited by two hydrophobic edge strips 50. The sample liquid applied to the front side of the test field 32 wets the test strip 48 in the form of a sample spot 52 which is scanned from the transparent rear side of the tape by the light spots 36', 38', 40' of the light-emitting diodes 36, 38, 40 in the measuring position on the deflecting tip 34. However, since the tape can be transported only in one direction (arrow 54) the check fields 44, 46 are firstly detected before the actual measurement as elucidated in more detail in the following.

The white field 46 of the yet unused tape section 42 is located on the deflection tip 34 in front of the measuring unit 18 in the stand-by position. The white field 46 printed onto the carrier tape 34 in white paint is of such a size that the measuring window detected by the measuring unit 18 is completely covered. It is also possible to position an upstream black field 44 for measurement before taking up the stand-by position.

Figure 4:
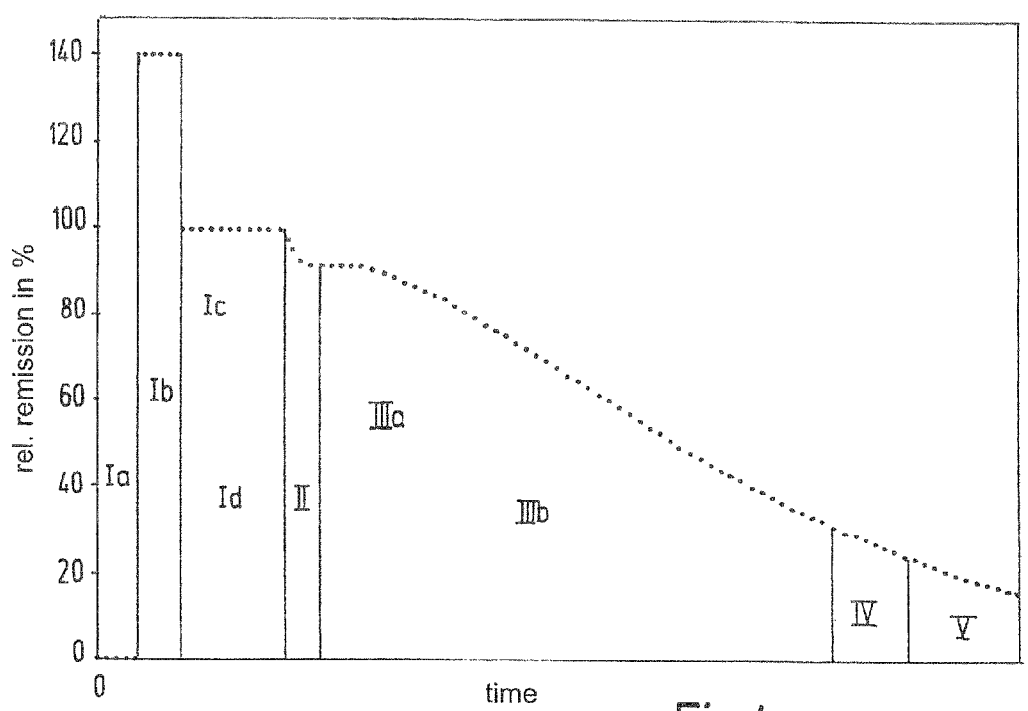
FIG. 4 shows a measured value diagram in various phases of the measurement process.

As shown in FIG. 4 the measurement cycle for each tape section 42 is divided into various phases. In phase Ia the black field 44 is scanned in order to detect contamination and optionally for self correction by the device as will be elucidated in more detail in the following. In phase Ib the white field 46 is measured to check tape quality and optionally for self correction. In phase Ic a so-called dry blank value DBV is determined on the yet unused test field 32. Then the user is prompted to apply blood (Id). This ends the preparation phase.

In phase II a wetting detection is carried out on the test field 32 by means of the IR light-emitting diodes 36, 40. The signal intensity decreases when the test strip 48 is wetted.

Subsequently the kinetics of the analyte-specific measurement signal is monitored on the bases of the colour change of the test strip 48 in phases III and IV at a measurement interval of for example 0.2 s. The end phase IIIb of the monitoring of the kinetics is reached when the diminishing signal change that depends on the chemical reaction rate reaches a termination threshold. Then a duplicate measurement takes place using LED 38 in phase IV in order to determine an averaged end value EV. The glucose concentration is then determined in relative remission by calculating a quotient from this end value EV and the dry blank value DBV (in general the relative remission is calculated from the ratio of the actual measured value to the dry blank value). In addition in phase V a homogeneity measurement of the sample spot 52 is provided to detect underdosing which is based on a quantitative signal comparison of the two IR-LEDs 36, 40. Finally the glucose concentration is shown to the user in the display of the device 10.

Apart from the actual measurement for determining the glucose concentration, the functions or fail safes mentioned above are put into practice as follows:

The contamination detection takes place using LED 38 after inserting the cassette 12 and following each glucose measurement by measuring the signal offset on the black field 44. This offset is generated by the entire measurement environment with the LEDs switched on without involvement of a test. It is thus an additive quantity when determining the measured value. The emitted light is partially reflected and passed to the detector 41 as a result of contamination or other optical changes in the optical path for example due to foreign bodies, dust and scratches. In the offset detection the black field 44 serves as a substitute for a black hollow space which does not reflect any light. Basically it would, however, also be possible to carry out a measurement through the transparent carrier tape into the dark interior space of the device.

The detected signal offset is compared with the threshold value stored in the device 10 which was determined during the product manufacture as a lot mean. If the deposited threshold value is exceeded, then an error message is triggered.

In order to check the quality of the tape cassette 12 used possibly after a long storage period as a disposable article, a reference value WF is recorded at least on the first white field 46 on the test tape 14. Subsequently potential damage to the test strip chemistry for example due to environmental effects is detected by a corresponding change of the dry blank value DBV of the first test field 32. For this purpose the absolute remission value is not used but rather the relative remission value based on the reference value WF.

A corresponding lot control value CC is determined during a batchwise production of test tapes 14 by measuring test fields 32 and white fields 46 on the test tape material. The tape is manufactured in a roll-to-roll process which allows such a control value assignment to a substantially uniform coating. The lot control value is stored in an RFID chip 56 on the cassette 12 and read out and processed by the device electronics 20. The RFID chip 56 is attached to the outside of the cassette 12 and is only shown symbolically in the cut open diagram of FIG. 2.

The test field quality check is negative when the following condition is fulfilled:

$$DBV_1/WF_1 < CC - \Delta C \qquad (1)$$

in which $\Delta C$ is a tolerance value and the index 1 refers to the first tape section 42. In this case a corresponding error message is issued and the cassette 12 is discarded if necessary.

If the result is positive it is also possible to carry out a quality check for subsequent tests within narrow limits. For this purpose the relative remission value $C_{n-1}$ of the currently used test field is stored in a device memory and used instead of the lot control value CC in accordance with the above-mentioned equation (1). Hence, a subsequent quality check of a next test field n is negative when:

$$DBV_n/WF_n < C_{n-1} - \Delta C \qquad (2).$$

In general a calibration of the devices 10 by the manufacturer ensures that relevant measured values can only be generated in the specified measuring range of all opto-electronic components. In this case the electrical parameters of the three LEDs 36, 38, 40 and the optical parameters are calibrated.

A self-correction process or a calibration by the device is in principle also possible in order to minimize the specific effect of the signal offset and varying absolute measurements on the measured value determination. The optical offset varies from cassette to cassette for manufacturing reasons. In addition a spacing component subject to tolerances occurs due to the separation of the instrument optical system and tape guidance by the cassette.

The black and white fields 44, 46 which are located on the test tape 14 in front of each test field 32 are in turn used for the reference measurement. These fields are already measured during the manufacture and provided with a lot mean value. These values are then stored on the RFID chip 56 as a reference value.

The black field value measured on the first black field 44 after inserting a cassette 12 is checked to see whether it is near to the manufacturer's lot mean value for the optical offset within a specified tolerance. If this is the case, the lot mean value is retained. If the measured black field value deviates from this tolerance range, the difference to the lot mean value is determined and added to the optical offset. The optical offset is subtracted from the gross measurement signals obtained subsequently on the test fields 32.

However, the correction of the optical offset is only carried out up to a defined limit. When this limit is exceeded an error message is triggered as described above. The black field measurement is used before each subsequent test only to detect contamination.

In the case of the white field calibration, the individual sensitivity value of the cassette is determined by comparing the measured value recorded on the white field 46 with the lot mean value stored on the RFID chip 56 as an absolute remission. If the measured white field value $m_K$ is near to the lot mean value in within a tolerance range, then the lot mean value $m_w$ is used for a subsequent scaling of the offset-corrected gross measurement signal and otherwise the individual cassette sensitivity $m_K$ is used. However, an error message is sent out when a threshold value for deviation is exceeded.

In order to substantially exclude an unintentional generation of a measured value due to operating errors, it is possible to determine a control value from a time-dependent and/or wavelength-dependent change in the measurement signals in which case the measurement signals can then be further processed as valid or be rejected as erroneous depending on a threshold value of the control value.

A first such fault can be that due to the distance-dependency of the measuring principle an artificial measuring result could be generated by pressing against the deflecting tip 34 without a sample having been applied. In order to exclude this, measurement signals are recorded on the test field 32 at two different wavelengths and the control value is determined from a difference in the signals of the measurement signals at different wavelengths.

Figure 5:
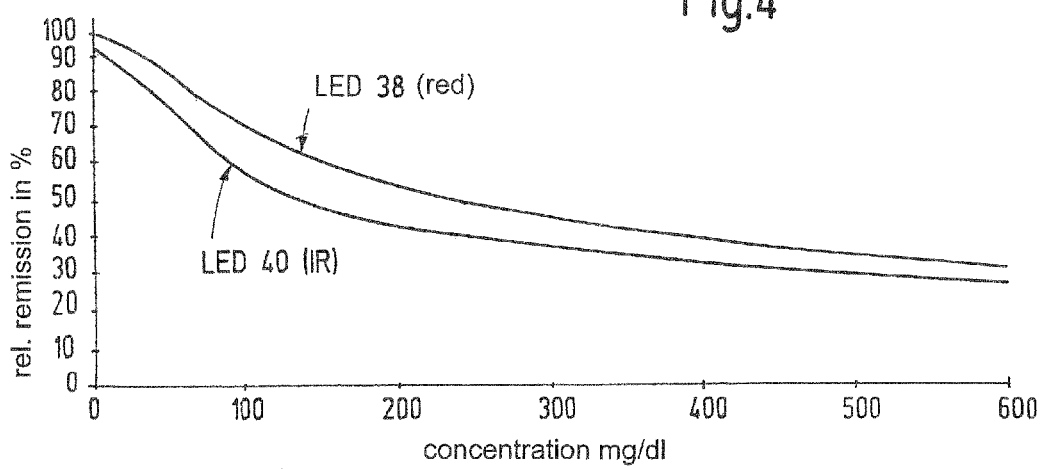
FIG. 5 shows a measured value diagram as a function of the concentration of an analyte for two different wavelengths.

As shown in FIG. 5 when a sample is measured using different wavelengths this results in different values for the relative remission over the entire range of the analyte or glucose concentration to be analyzed. This difference in signals arises due to the wetting of the test field 32 with the body fluid (hence a difference is found even at a sample concentration of zero) and strengthens when the test chemistry system forms an intensified reaction colour. If a measurement signal can be generated only by pressing, the typical difference in the LEDs 38, 40 at different wavelengths cannot be observed due to the absence of wetting and the absence of reaction colour by which means a fault is detected. The specified threshold value of the signal difference can for example be at 3% relative remission.

Another scenario for an unintentional generation of measured values is that an erroneous detection of an application of blood is provoked by a shift in the tape. If a dark edge strip 50 of the test field 32 is shifted into the optical path of the measuring unit 18 by a user manipulation, high measured values can be generated without a sample having been applied.

Typical reaction kinetics of blood samples on a test field 32, however, exhibit a signal amplitude of about 10% above about 100 mg/dl glucose concentration as determined as the difference between the first and last kinetic measurement in phase III (FIG. 4). If in contrast the test tape is merely shifted in phase II as described above, there is an abrupt darkening and afterwards a constant signal i.e. variable reaction kinetics and an appreciable signal amplitude are not observed in phase III. Thus, an error can be detected by determining the control value from a signal difference of signals measured at the beginning and end of a measurement interval and detecting a fault when the signal difference is almost zero.

If a test field 32 is located in front of the optical system 43 in the state of sample application detection (phase II in FIG. 4), the control device 20 of the instrument 10 interprets a change in signal by a specified amount as a sample application and starts the analysis. High air humidity as well as exposure to sunlight could already lead to such a signal change without sample application under unfavourable circumstances and thus result in a start of the measurement.

In order to prevent this the time course of the change in blank signal is checked in the state of awaiting the sample. Whereas application of a blood sample already leads to a decrease in remission of several percent within half a second, such a decrease is only achieved over a period of more than 20 seconds upon exposure to sunlight or air humidity. Consequently it is possible that periodic blank values are recorded periodically on the test field provided for the sample application and that the control value is determined from a change in the blank value compared to an initial blank value where an application of liquid is detected when the change in the blank value is above a predetermined threshold value (of for example about 5%) and a fault is detected when it is below this value if necessary after a specified waiting time.

Another measurement problem can be that the dry blank value of a test field 32 that is provided but is still unused, is for example changed by the effect of light or moisture and thus results in a falsification when used as a reference value for the determination of the relative remission. The measured value of the unused test field can therefore be checked periodically in the state of awaiting a sample and either be updated in order to prevent falsifications of the measured value or in order to abort the measurement with an error message above a certain limit value of for example more than 0.5%/s relative remission change.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A method of detecting body fluid sample application error on a test tape having a plurality of test fields, the method comprising the steps of:

applying the body fluid sample to a test field of the test tape to initiate a test, wherein the test tape is in a test device having a measuring unit comprising at least one radiation source to generate at least one wavelength of light and a photodiode for reflection-photometric signal detection of the at least one wavelength of light;

photometrically scanning the test field at a first wavelength of light and a second wavelength of light with the measuring unit and detecting relative remission measurement signals of the first wavelength of light and the second wavelength of light over a duration of a measurement interval, wherein the first wavelength of light is a visible range wavelength and the second wavelength of light is an infrared range wavelength;

calculating a control value based upon a measurement signal difference between relative remissions of the first wavelength of light and the second wavelength of light, wherein the measurement signal difference between the first wavelength of light and the second wavelength of light results from wetting the test field with the body fluid sample; and detecting body fluid sample application error and discarding the test if the control value is below a preset threshold at a beginning of the measurement interval.

2. The method of claim 1, wherein the first wavelength is about 650 nm and the second wavelength is about 875 nm.

3. The method of claim 1, wherein the preset threshold is about 3% relative remission.

* * * * *